(12) United States Patent
Ellenbogen

(10) Patent No.: US 7,661,821 B2
(45) Date of Patent: Feb. 16, 2010

(54) APPARATUS FOR IMPROVING VISUAL PERCEPTION

(75) Inventor: Nir Ellenbogen, Singapore (SG)

(73) Assignee: RevitalVision, LLC, Lawrence, KS (US)

( * ) Notice: Subject to any disclaimer, the term of this patent is extended or adjusted under 35 U.S.C. 154(b) by 103 days.

(21) Appl. No.: 12/083,533

(22) PCT Filed: Oct. 15, 2006

(86) PCT No.: PCT/IL2006/001173

§ 371 (c)(1),
(2), (4) Date: Apr. 14, 2008

(87) PCT Pub. No.: WO2007/043047

PCT Pub. Date: Apr. 19, 2007

(65) Prior Publication Data

US 2009/0109398 A1    Apr. 30, 2009

Related U.S. Application Data

(60) Provisional application No. 60/726,157, filed on Oct. 14, 2005.

(51) Int. Cl.
*A61B 3/02*    (2006.01)
*A61B 3/00*    (2006.01)

(52) U.S. Cl. .......... 351/243; 351/246; 351/203
(58) Field of Classification Search ......... 351/200–246; 382/128, 114; 600/300, 558
See application file for complete search history.

(56) References Cited

U.S. PATENT DOCUMENTS 7,427,138 B2 * 9/2008 Ellenbogen ................. 351/243

* cited by examiner

*Primary Examiner*—Mohammed Hasan

(57) ABSTRACT

Apparatus for improving the visual perception ability of a person with respect to a particular eye condition of at least one eye, includes a client terminal including display device for displaying images to the person, and an input device for inputting responses by the person to images displayed in said display device; and a processor system programmed such that in an evaluation phase, the processor controls said display device to display to the person a plurality of images selected to test the visual perception ability of the person with respect to at least one visual defect, and utilizes responses inputted by the person via said input device to select another plurality of images designed to improve the visual perception ability of the person with respect to a detected visual defect.

20 Claims, 7 Drawing Sheets

APPARATUS FOR IMPROVING VISUAL PERCEPTION

RELATED APPLICATIONS

This Application is a National Phase of PCT Patent Application No. PCT/IL2006/001173 having International filing date of Oct. 15, 2006, which claims the benefit of U.S. Provisional Patent Application No. 60/726,157 filed on Oct. 14, 2005. The contents of the above Applications are all incorporated herein by reference.

FIELD AND BACKGROUND OF THE INVENTION

The present invention relates to apparatus for improving visual perception. The invention is particularly useful for improving visual perception in accordance with the method and apparatus described in U.S. Pat. Nos. 6,876,758 and 7,004,912, and in International Patent Application PCT/IL2004/001012, published as WO 2005/044096, the disclosures of which are incorporated herein by reference, and therefore the present invention is described particularly with respect to such methods and apparatus.

SCIENTIFIC BACKGROUND

The visual system is a highly sophisticated optical processing mechanism, classically described as a hierarchy of visual processing stages (though recent views emphasize backward projections), starting from light detection and transduction in the eye (i.e. photoreceptors) through several stages of spatial integration, each stage forming receptive fields of increasing complexity.

Not all components imaged on the retina are equally perceived; some are constrained by the efficiency of neural processing in the brain. An important stage in image analysis in the primary visual cortex involves receptive fields (units) sensitive to image contrast that varies in a specific direction (orientation selectivity) on a specific scale (size selectivity). Human contrast sensitivity is best described by the aggregate response of these units (filters).

Cortical cells (neurons) are highly specialized and optimized as image analyzers, so they respond only to a limited range of parameters (filters) of the visual image, such as orientation, location in the visual field, and spatial frequency. Thus, to characterize an image, visual processing involves the cooperative activity of many neurons. These neural interactions contribute both excitation and inhibition. Spatial interactions between oriented receptive fields are an important factor in modulating activity of the corresponding neuronal units.

Contrast is one of the most important parameters activating cortical cells involved in vision processing. Responses of individual neurons to repeated presentations of the same stimulus are highly variable (noisy). Noise may impose a fundamental limit on the reliable detection and discrimination of visual signals by individual cortical neurons. Neural interactions determine the sensitivity for contrast at each spatial frequency, and the combination of neural activities set the Contrast Sensitivity Function (CSF). Theory suggests that the relationship between neuronal responses and perception are mainly determined by the signal-to-noise ratio (S/N ratio) of the neuronal activity. The brain pools responses across many neurons to average out noisy activity of single cells, thus improving the signal-to-noise ratio, leading to substantially improved visual performance.

In several studies, it has been shown that the noise of individual cortical neurons can be brought under experimental control by appropriate choice of stimulus conditions: Kasamatsu, T., Polat, U., Pettet, M. W. & Norcia, A. M. Colinear Facilitation Promotes Reliability of Single-cell Responses in Cat Striate Cortex. Exp Brain Res 138, 163-72. (2001); and Polat, U., Mizobe, K., Pettet, M. W., Kasamatsu, T. & Norcia, A. M. Collinear Stimuli Regulate Visual Responses Depending on Cell's Contrast Threshold. Nature 391, 580-4 (1998). Such studies also show that contrast sensitivity at low levels can be increased by a factor of 2 through control of stimulus parameters. At the neural level, the improvement in sensitivity would not be expected or largely reduced without a concurrent decrease in response noise. This precise control of stimulus conditions leading to increased neuronal efficiency is fundamental in initiating the neural modifications that are the basis for brain plasticity.

Brain plasticity relates to the ability of the nervous system to adapt to changed conditions, sometimes after injury or strokes, but more commonly in acquiring new skills. Brain plasticity has been demonstrated in many basic tasks, with evidence pointing to physical modifications in the adult cortex during repetitive performance. Several studies demonstrate the plasticity of neural interactions resulting from repetitive performance of specific visual tasks leading to improved visual performance. The improved visual functions, like skill learning, were retained after a few years of retesting. Both an increased range of excitatory interactions and reduced inhibition were observed in subjects with normal vision, and in monkeys. These studies point to activity-dependent plasticity of the visual cortex, where the specific connections activated throughout repetitive performance are modified, leading to improved performance.

The technology in the above-cited related applications probes specific neuronal interactions, using a set of patient-specific stimuli that improve neuronal efficiency and induce improvement of CSF due to a reduction of noise and increase in signal strength—followed by a marked improvement in spatial resolution (Visual Acuity).

"Lateral Masking": Modulation of CSF

The typical building block of the visual stimulations is the Gabor patch (FIGS. 1a and 1b). "Gabor Patches" are widely used in the field of visual neuroscience. They have been shown to efficiently describe and match the shape of receptive fields of neurons in the primary visual cortex and thus represent the most effective stimulation.

The set of Gabor functions is defined as a collection of odd (sine) and even (cosine) wave functions with limited spatial extent (and/or temporal extent).

$$Go(x,y)=Ao\exp(-((x-xo)2+(y-yo)2)/\sigma2)*\sin(2\pi/\lambda*(x\cdot\cos(\theta)+y\cdot\sin(\theta)))$$

Contrast response of a single neuron can be modulated by activity of neighboring neurons, as shown by single-unit recordings of neuronal activity in the visual cortex of cats and monkeys.

Recent research by Polat, U., Mizobe, K., Pettet, M. W., Kasamatsu, T. & Norcia, A. M., conducted invasively, utilizing cat subjects, demonstrated the linear relationship between contrast and neuronal response (green line) as shown in FIG. 2. Research published in Nature in 1998 revealed a non-linear response to the same target when surrounded by flanking images (blue line). These flanking images where found to increase response (facilitation) at lower contrast levels and decrease response (suppression) at higher contrast levels. This fundamental discovery regarding the neural connections responsible for vision in cats is also fundamental to the techniques involved in the present invention for vision improvement in humans.

It has been demonstrated that contrast sensitivity of adult human subjects at low levels can be significantly increased through specific control of the Gabor patches parameters. This stimulation-control technique, where collinearly-oriented flanking Gabors are displayed in addition to the target gabor image, is called "Lateral Masking".

The results shown in FIGS. 3 and 4 are derived from subjects (adults) with normal vision, who were exposed to psychophysical tasks using the lateral masking technique:

When subjects practice contrast modulation under a very precise and subject-specific stimuli regimen, a dramatic improvement in contrast sensitivity is achieved. The improvement in contrast sensitivity induces also an improvement in visual acuity.

When utilized and adapted to each individual, this technique is effective in improving the vision of persons with several eye conditions, including but not limited to: (1) Amblyopia, (2) Myopia, (with or without Astigmatism) (3) Presbyopia, (4) Hyperopia, (5) Emmetropia, (for obtaining super-normal vision) (6) Ammetropic post refractive surgery patients, (being left with residual refractive errors), and (8) Eye diseases causing reduced vision, such as glaucoma or age-related macular degeneration (AMD). It may also be used to reduce progression of myopia in childhood.

OBJECT AND BRIEF SUMMARY OF THE PRESENT INVENTION

An object of the present invention is to provide apparatus for improving visual perception, which apparatus provides a number of advantages as will be described more particularly below.

According to a broad aspect of the present invention, the provided apparatus for improving the visual perception ability of a person with respect to a particular eye condition of at least one eye, comprising: a client terminal including a display device for displaying images to the person, and an input device for inputting responses by the person to images displayed in the display device; and a processor system programmed such that in an evaluation phase, the processor controls the display device to display to the person a plurality of images selected to test the visual perception ability of the person with respect to at least one visual defect or inefficiency, and utilizes responses inputted by the person via the input device to select another plurality of images designed to further test the visual perception ability of the person with respect to at least one visual defect or inefficiency, and in a treatment phase, the processor controls the display device to display to the person the another plurality of images to thereby improve the visual perception ability of the person with respect to the detected visual defect or inefficiency, and utilizes responses inputted by the person via the input device to select another plurality of images designed to further improve the visual perception ability of the person with respect to the detected visual defect or inefficiency; characterized in that the display device is a head-wearable display wearable over the eyes of the person and controlled by the processor system to display the plurality of images during both the evaluation phase and the treatment phase.

According to additional features in the preferred embodiment of the invention described below, the head-wearable display further includes earphones to be located over the ears of a person, and also controlled by the processor system to provide audio information to the person regarding the images displayed.

An embodiment is described below wherein the apparatus further includes training glasses to be worn by the person and having a reduced refraction with respect to at least one eye of the person; and the head-wearable display further includes a holder for holding the training glasses in front of the at least one eye of the person during the treatment phase.

According to still further features in the described preferred embodiment, the processor system includes a client processor in the client terminal, and a host processor in a host server serving a plurality of clients terminals; and the client processor and the input device are included in a hand-held portable unit. The client processor communicates with the head-wearable display via a wireless communication channel. The client processor also communicates with the input device via a wireless communication channel.

In the described preferred embodiment, the head-wearable display further includes earphones to be located over the ears of a person and also controlled by the client processor to provide audio information to the person regarding the images displayed; and the client processor also communicates with the earphones via a wireless communication channel. The client processor communicates with the host processor via the Internet.

It will thus be seen that the apparatus constructed in accordance with the foregoing features is much more conveniently usable at any convenient time or location, and does not require the user to visit or spend time in a clinic or other treatment center. However, using a head-wearable display provides a number of important benefits, including standardizing the quality of the display; the treatment environment such as lighting conditions, contrast, brightness, etc., and the distance between the eyes and the display. Many types of head-wearable displays are commercially available and may be used, such as head-mounted displays, goggles, or glasses, which superimpose images or data to be viewed simultaneously with the normal field viewed by the user. The client processor may be a PDA, cellular phone, laptop or desktop computer, or other mobile computing unit. Communication between the wearable display and the portable processing unit may be wired or wireless (e.g., sonic, infra-red, radio, Bluetooth). The responses elicited from the user may be inputted via a keyboard, touch-screen, stylus-screen, or voice-activated input device, etc.

When training glasses or lenses are to be used, they may be training glasses worn under the wearable display device, lenses slidable in slots in goggles, contact lenses worn under the wearable display device, etc.

According to the preferred embodiments of the invention described below, the treatment phase includes a plurality of treatment sessions in each of which are displayed to the person a plurality of images designed to elicit responses to be used for selecting the plurality of images in a subsequent treatment session such as to progressively improve the visual perception ability of the person with respect to the detected visual defect. After at least one treatment session where training glasses are used, the refraction of the training glasses is increased or decreased for the next treatment session as determined in order to progressively improve the visual perception ability of the person with respect to the detected visual defect. At least one predetermined parameter of the plurality of images displayed in one treatment session is varied in the subsequent treatment session.

More particularly, in the described preferred embodiments, the treatment phase includes a plurality of treatment sessions each of which includes a plurality of visual perception tasks. In each such task there is displayed to the person at least one image including stimuli designed to elicit a response useful for selecting at least one other image to be displayed in the subsequent visual perception task of the respective treatment session such as to progressively improve the visual perception ability of the person with respect to the detected defect.

In one described preferred embodiment, the visual perception tasks in at least some of the sessions in the treatment phase include spatial frequency changes in which the spatial frequency of the stimuli is changed. As described, the spatial frequency is changed starting with lower spatial frequencies and progressively moving to higher spatial frequencies.

In another described preferred embodiment, in at least some of the sessions in the treatment phase, the orientation of the stimuli is changed. The described preferred embodiment is one wherein the eye condition includes astigmatism characterized by a distortion area in an astigmatic zone; and wherein, in at least some of the treatment sessions in the treatment phase, the orientations of the stimuli are changed by progressing towards the distortion area in the astigmatic zone.

In all the described preferred embodiments, the treatment phase includes a sufficient number of treatment sessions to improve the person's sensitivity contrast function by the person achieving a desired range of contrast levels.

Further features and advantages of the invention will be apparent from the description below.

BRIEF DESCRIPTION OF THE DRAWINGS

The invention is herein described, by way of example only, with reference to the accompanying drawings, wherein.

Figure 1:
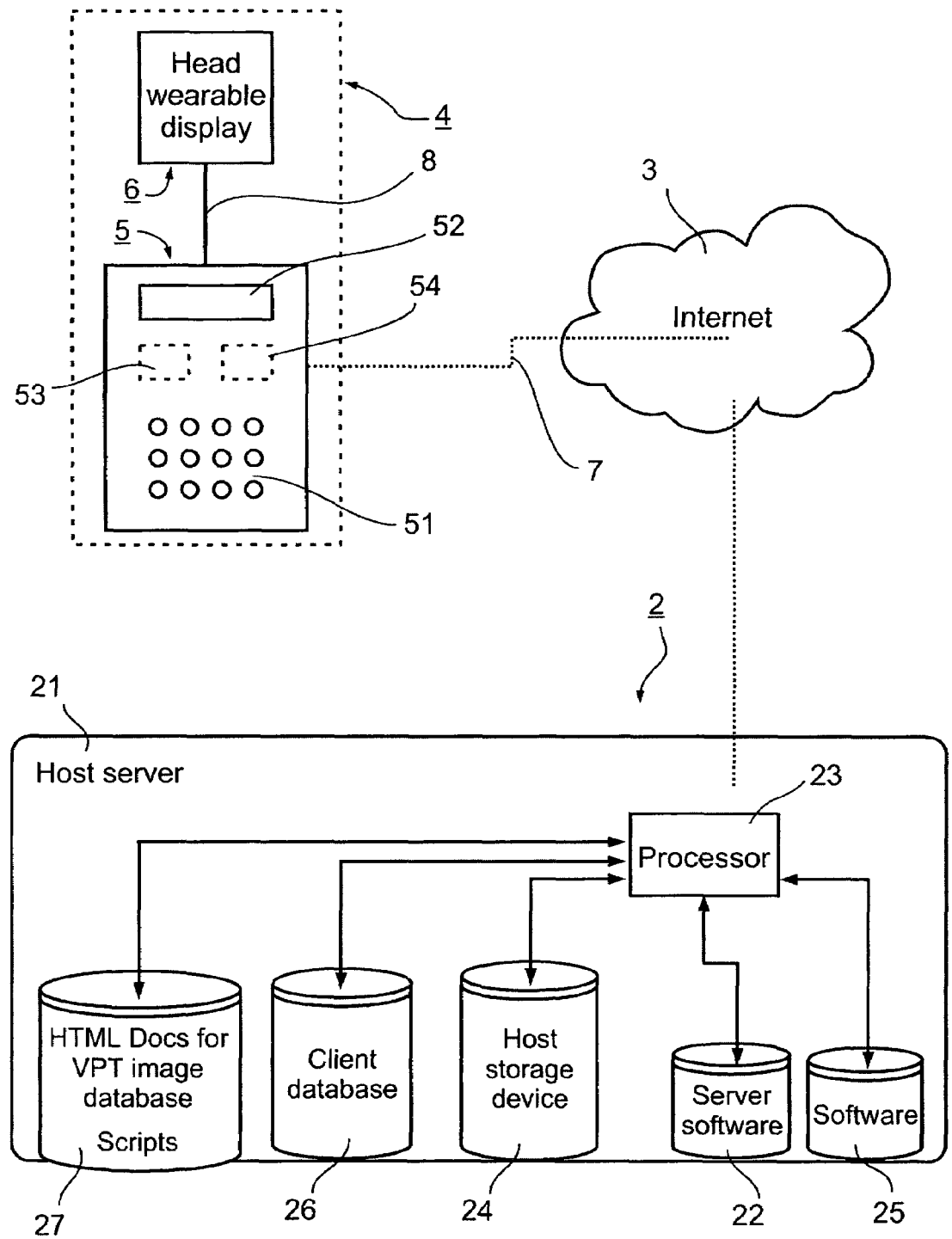
FIG. 1 is a block diagram illustrating the architecture of one system constructed in accordance with the present invention.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Treatment Concept

Overview

As will be described more particularly below, the present invention involves a computerized interactive treatment in which the patient is exposed to a series of psychophysical visual tasks—"Visual Perception Tasks (VPT)". A VPT aims to measure or improve a person's visual perception process. In fact, each VPT is generally designed to target a specific aspect of the visual perception process.

The various VPT's implemented by the system have structuring for performing all the following operations:

i. Providing a patient with visual stimuli designed to stimulate one or more areas of the patient's visual cortex;

ii. Receiving responses to the visual stimuli from the patient using an input device (e.g., the computer mouse); and then iii. Providing more visual stimuli based on responses to the previous visual stimuli, until a threshold level is reached.

The treatment is administered in successive 30-minute sessions, each session comprised of a series of VPT's., 2-3 times a week for a total of approximately 30 sessions.

As each patient suffers from individual specific neural capabilities, the treatment is personalized—specifically tailored to each individual subject. Subject specificity is achieved by the following measures:

1. Analysis and identification of each subject's neural deficiencies or inefficiencies or within normative range capabilities through performance of a set of visual perception tasks to which the subject is exposed. This stage is called the computerized evaluation stage, and is usually comprised of up to three sessions. As a result, a treatment plan is defined.

2. Based on said analysis, administering patient-specific stimuli in a controlled environment. The visual stimuli parameters are algorithmically controlled and tailored to each subject's needs in order to address and improve the identified neural deficiencies or inefficiencies or enhance the neuronal activity beyond the normative range. This is the treatment stage and is usually comprised of approximately 30 to 50 treatment sessions, depending on each individual performance.

Each treatment session is designed to train, directly and selectively, those functions in the visual cortex that were diagnosed to be potentially enhanced. During each session an algorithm analyzes the patient's responses and accordingly adjusts the level of visual difficulty to the range most effective for further improvement.

Between sessions, the performance and progress of the patient are measured and taken into account by the algorithm for the definition of the visual stimuli parameters of the next therapeutic session. Thus, for each subject an individual training schedule is designed based on the initial state of visual performance, severity of dysfunction and progress in therapeutic training.

The visual stimuli parameters are algorithmically controlled and tailored to each subject's needs. Among these parameters are: Spatial Frequencies, Spatial arrangement of the stimuli, Contrast level, Orientation (local and global), Tasks Order, Context and Exposure Timing.

The foregoing treatment may be used to improve vision of subjects with several eye conditions, including but not limited to: (1) Amblyopia, (2) Myopia, (with or without Astigmatism) (3) Presbyopia, (4) Hyperopia, (5) Emmetropia, (for obtaining super-normal vision) (6) Ammetropic post refractive surgery patients, (being left with residual refractive errors), and (8) Eye diseases causing reduced vision, such as glaucoma or age-related macular degeneration (AMD). It may also be used to reduce progression of myopia in childhood.

Treatment Principles

Image quality is determined by the quality of the optics (the eye) and the efficiency of the neural processing. This treatment aims to improve the quality of vision by optimizing and enhancing the neural processing in the visual cortex.

This is mainly achieved by improving the lateral interactions among neurons in the visual cortex, increasing the S/N ratio, and improving the contour integration and spatial localization.

This is done through performing Visual Perception Tasks (VPTs) focusing in reduction of the lateral inhibition and increase of lateral excitation. Practicing the lateral interactions leads to an increased range of those interactions.

Through the personalized treatment sessions, the size (spatial-frequency) and orientation of the stimuli are changed, starting with lower spatial-frequencies and progressively moving to the higher ones, with four or more orientations at each size.

The trained spatial frequencies are selected according to the level of inefficiency, which is measured during the computerized evaluation.

For optimal improvement, the achieved contrast thresholds should enter into a contrast funnel. If contrast exceeds this funnel, the Gabor patches are elongated towards the local orientation axis, in order to decrease contrast thresholds.

Variability of lateral interactions along various orientations, which means unequal contrast response at various orientations is addressed by changing the orientation, starting with the easier one (at which lower contrasts are achieved) and progressively moving to the harder one.

The zone of suppression or facilitation receives high attention, as abnormal lateral interactions are expressed in increased suppression. The VPTs initially concentrate at the area of low suppression level. Upon improvement, and creation of a certain level of facilitation, the focus will gradually shift to the area of higher suppression level, which will follow to improve as well.

For persons with average lateral interactions, the focus is in improving the level of facilitation at the facilitation zone.

The treatment is performed using the best refractive correction for persons who suffer from reduced best corrected visual acuity (amblyopia) and for those who aim to improve their unaided vision (myopia, presbyopia), the treatment is performed with training glasses with increased or reduced refraction.

Training Glasses With Increased or Reduced Refractive Correction

For optimal improvement, the achieved contrast thresholds at any configuration (spatial frequency, orientation, exposure duration) should enter into a contrast funnel.

In order to keep the contrasts within the required range, the patients are preferably provided with training glasses with increased or reduced refractive correction.

The refraction value of the training glasses is determined according to the training eye decision (left, right or both eyes), the uncorrected visual acuity in the respective eyes and patient's refraction. This decision may be changed in the course of treatment based on the achieved contrast levels.

The provided training glasses refraction would be around the person's best refractive correction at, but not limited to the interval of ±0.5 diopter (D) or ±1.0 diopter (D).

Further details as to the various treatments that may be involved are described in the above-cited U.S. Pat. Nos. 6,876,758 and 7,004,912, and International Application PCT/IL 2004/001012 (WO 2005/044096), the disclosures of which are incorporated herein by reference.

A Preferred Hardware and Software Implementation

The accompanying drawings illustrate a preferred hardware and software implementation of the invention as described above.

The hardware implementation illustrated in FIG. 1 includes a host server 2 communicating via a global communications network, such as the Internet 3, with a plurality of client terminals 4. Host server 2 is typically a computer system 21 on a network with server software 22 configured to receive and answer requests for information. Typically, computer system 21 is also dedicated to storing data files and managing network resources, including network traffic. Computer system 21 generally includes a processor 23 and a data storage device 24.

Host server 2, through processor 23, has access to software 25 comprising sequences of instructions that cause processor 23 to perform a number of acts in accordance with the preferred methods described herein. Host server 2 also has access to a client database 26 that stores information concerning persons of the system. This information can include identification information and data relating to a person's performance during past VPT Sessions as indicated at 27. Client database 26 may reside outside host server 2, such as at client terminal 4.

Client terminal 4 is a remote terminal that provides an interface for a person to access host server 2. Client terminal 4 typically includes a computer system communicatively coupled to host server 2 by a communication network, such as the Internet 3. Its computer system generally includes a processor, a data storage device, a display screen, an input device, and software comprising sequences of instructions that cause the processor to perform a number of acts in accordance with the methods described herein.

According to the illustrated embodiment of the present invention, the client terminal 4 is constituted of two units, namely a computer unit 5 and a head-wearable display unit 6. Computer unit 5 is preferably a portable hand-held unit, such as a PDA, cellular telephone handset, laptop computer, or the like. It communicates with the Internet 3 via a communication channel 7, which is preferably a wireless channel, and also communicates with the head-wearable display unit 6 via a channel 8, which is preferably also a wireless channel. Such an arrangement thus enables each user to avail himself or herself of the treatment provided by the apparatus for improving visual perception at a time or location convenient to the user, and thus frees the user from having to visit or spend time in a clinic or other treatment center.

Computer unit 5 includes an input device, such as a keyboard 51, a display screen 52, a data storage device schematically indicated at 53, and a processor schematically indicated at 54, a pre-programmed or programmable by suitable software to perform a number of functions involved in improving visual perception, as will be described more particularly below. The head-wearable display unit 6 may be any one of the many known, such as head-up displays, goggles, eyeglasses, which project an image or data into the normal view of the user, so that the image or data is superimposed on the field of view seen by the user. The image or other information to be displayed is transmitted by the computer unit 5 via channel 8. Preferably, the head-wearable display unit 6 also includes earphones to be located over the ears of the person wearing the display unit 6 to provide audio information, also transmitted by the computer unit 5, regarding the images or other information displayed in unit 6.

Figure 2:
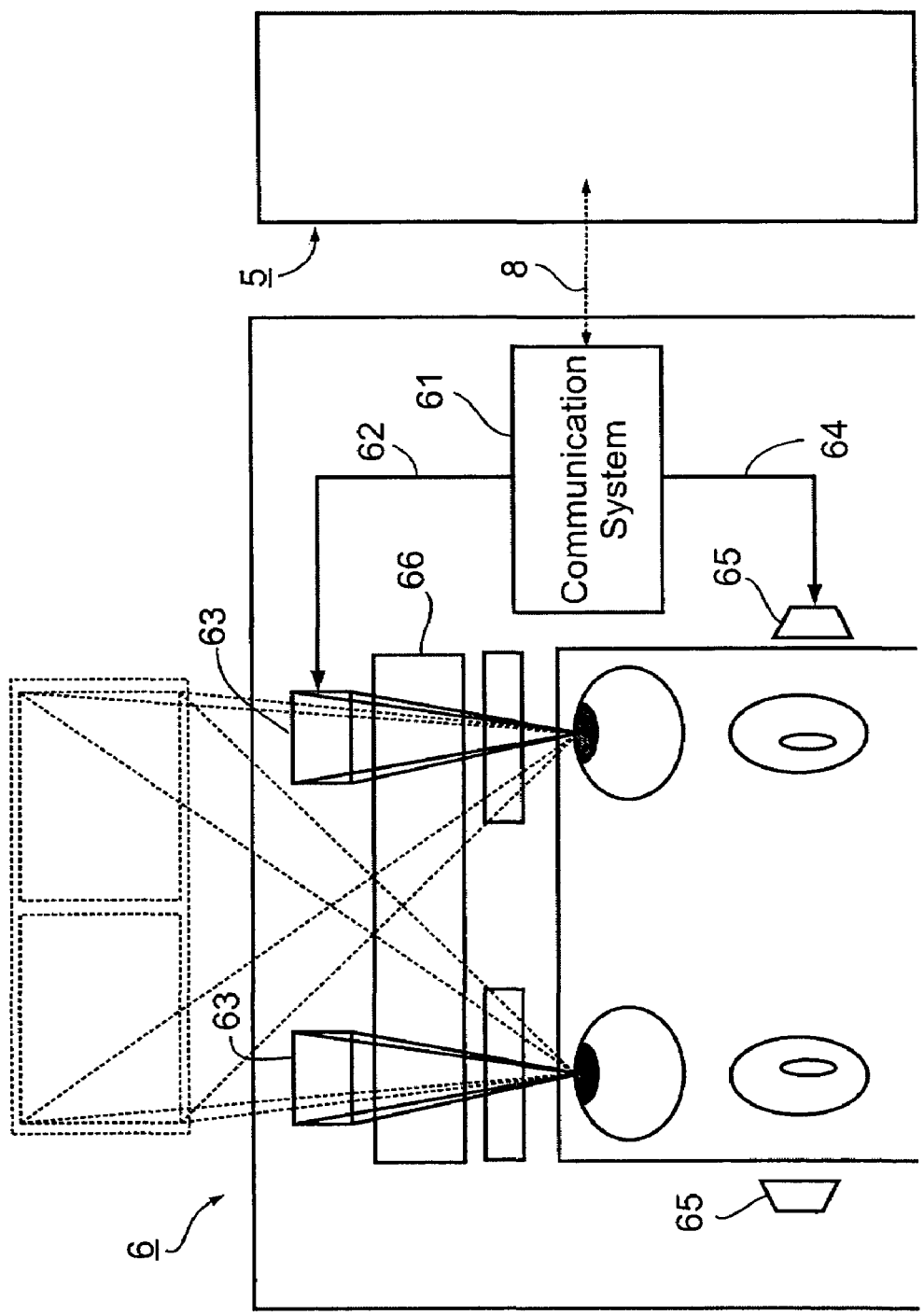
FIG. 2 is a block diagram more particularly illustrating the head-wearable display in the client terminal of FIG. 1.

FIG. 2 illustrates, for purposes of example, one construction of head-wearable display unit 6. It includes a communication system 61 receiving information from computer unit 5 via channel 8 which, as indicated earlier, is preferably a wireless channel, but may also be wired channel. The information received by communication system 61 consists of video information regarding the images to be projected into the field of view of the user, as well as audio information regarding the images so displayed to the user. The video information is fed via the video channel 62 to the two miniature display devices 63, each aligned with one of the eyes of the user; whereas the audio information is fed via audio channel 64 to a pair of earphones or speakers 65 alignable with the ears of the user. FIG. 2 also schematically illustrates the optical system at 66 between the two eyes of the user and the miniature display units 63 for superimposing the images appearing in the miniature display units 63 in the field of view of the user.

As indicated earlier, some treatments require that training glasses be worn by the user having a reduced refraction with respect to at least one eye of the user. For this purpose, the head-wearable display unit 6 further includes slots 66 between the user's eyes and the miniature displays 63, for receiving the lenses of the training glasses.

While FIG. 2 schematically illustrates one construction of head-wearable display which may be used, it will be appreciated that this is set forth merely for purposes of example, and that many other head-wearable displays could be used, for example eyeglasses as described in e.g., U.S. Pat. Nos. 6,349,001, 6,879,443, 6,629,076, or 6,005,536.

Figure 3:
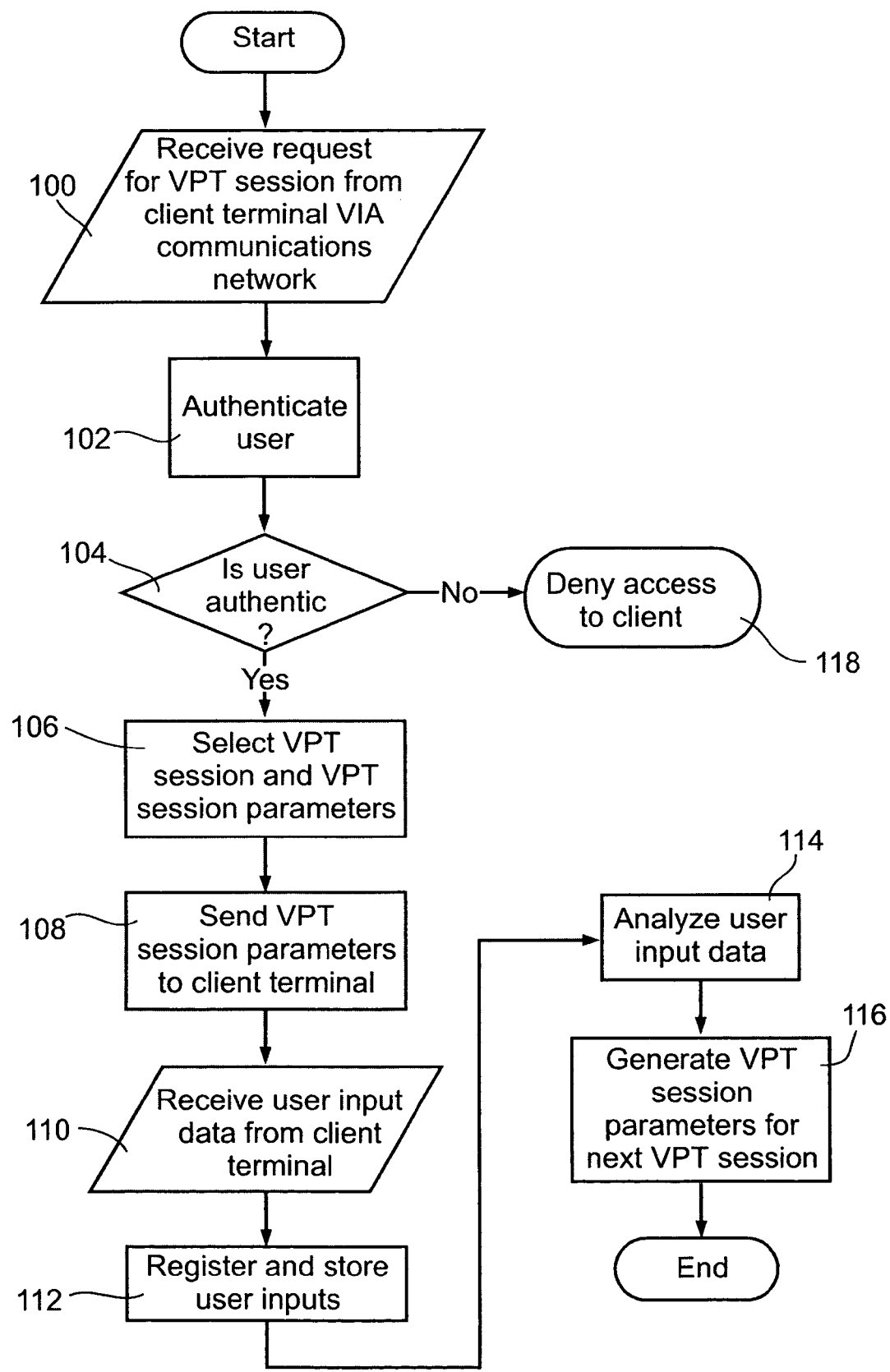
FIG. 3 is a flow chart illustrating the operations performed in a treatment session cycle.

FIG. 3 is a flowchart depicting a preferred implementation of how the method is carried out at host server 2. Starting with step 100, host server 2 first receives a request from client terminal 4 for access to a VPT Session. This request is sent from client terminal 4 to host server 2 over a communication network, such as the Internet 3.

In step 102, an authentication routine is performed to determine whether the request from client terminal 4 is valid. Generally, host server 2 does this by sending a request over the Internet to client terminal 4 for a username and password. In step 104, upon receiving the username and password data from client terminal 4, host server 2 compares that data to username and password data stored in client database 26. If host server 2 determines that the person is authentic, the process continues to step 106. If the person is deemed to be non-authentic, a message is sent to client terminal 4 informing the person that access to the VPT Sessions is denied, as shown in step 118. At that point, the person may be allowed to re-enter his or her username and password information a number of times.

In step 106, after host server 2 determines that the username and password supplied are genuine, a VPT Session is selected and an initial set of VPT Session parameters are generated. Typically, these parameters are defined in advance. The VPT Session is selected according to the methods described below, and the VPT Session parameters are generated as explained below with reference to step 116. The VPT Session parameters define items such as contrast level, contours, spatial frequency, distance between objects, target placement, local and/or global orientations, and presentation time for each of the VPTs and VPT Images being used to test or improve the visual perception process of the person.

In step 108, the initial VPT Session parameters are delivered to the client terminal 4 over the Internet 3. Software resident in computer 5 of client terminal 4 is configured to receive the VPT Session parameters and use them to dynamically generate VPT Images and VPTs. Once the parameters are delivered, the VPT Session can be carried out solely at client terminal 4 without the need for further interaction with host server 2. This preferred configuration allows the VPT Session to be administered to the person without delay or interruption.

In step 110, after the VPT Session has been administered to the person, host server 2 receives a set of person performance data from the respective client terminal 4. The person performance data is data relating to the person's performance, which primarily comprises the stabilized values generated for each series of VPTs administered during a VPT Session. It can also include some or all of the user inputs received by client terminal 4. The person performance data is generated by client terminal 4 and is then sent back to host server 2 over the Internet 3.

In step 112, host server 2 stores the person performance data it receives from client terminal 4.

In step 114, host server 2 analyzes the person performance data to reveal any visual perception deficiencies, and to determine the level of performance of the person's visual perception process. Software 25 provides instructions and data for processor 23 to carry out this analysis. This is done by comparing the person performance data to data collected from persons with "normal vision," i.e., based on generally acceptable levels of performance for each of the different aspects of the visual perception process; this helps gauge the person's level of performance. Processor 23 performs this comparison, using data related to that of a "normal observer," which is stored in data storage device 24.

In step 116, new VPT Session parameters are generated for use in the next VPT Session, based at least in part upon the person performance data received by host server 2, and upon the analysis conducted on the person performance data by processor 23. These new parameters again define specific VPT Images and VPTs to further improve the person's visual perception ability based upon the person's level of performance.

Figure 4:
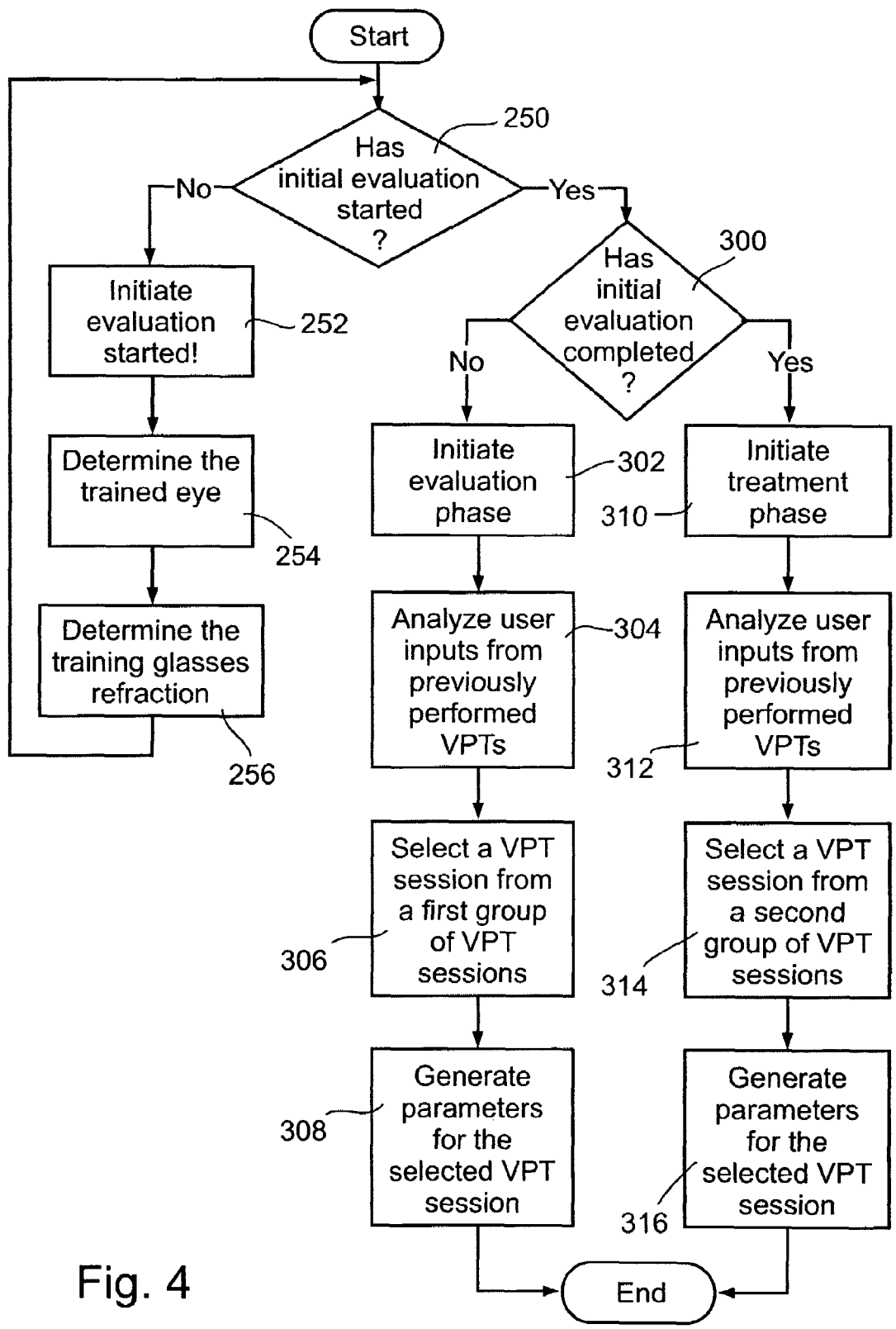
FIG. 4 is a flow chart illustrating the operations performed in a selected VPT (Visual Perception Task) session.

FIG. 4 illustrates a preferred method of determining the selected VPT session, wherein before the initial evaluation has started (steps 250, 252), a determination is made as to the type of training glasses to be applied to the patient during the treatment (steps 254, 256). As described earlier, training glasses with reduced refraction for the respective eye may be applied to the one or both eyes being treated, particularly when the eye condition being treated is myopia, with or without astigmatism. Thus, in order to keep the contrasts within the desired range, the patients would be provided with training glasses with reduced refractive correction.

As also described earlier, not only is the type of training glasses determined, but also the training eye is determined. During the treatment, eye swapping may be effected wherein the trained eye is changed to the left eye, the right eye, or both eyes. There is a logical dependency between the change of the training eye, the training glasses, and the spatial frequency. When the training eye is changed, the training glasses, as well as the spatial frequency, may also be changed.

There are two forms of VPT sessions available: an evaluation phase to ascertain a person's visual perception ability, and a treatment phase to improve the person's visual perception. Accordingly, as shown in step 300, the first step in selecting a VPT Session is to determine whether the person has undergone the evaluation phase. If an evaluation has not been completed, the next step in the process is to move on to step 302. Otherwise, the flowchart will continue at step 310.

Starting with the evaluation phase and step 302, a person undergoes an evaluation to ascertain the condition of the person's visual perception process. This data allows generation of effective VPTs that target the person's visual perception deficiencies. It also allows for a baseline set of data to gauge whether the person's visual perception is improving over the course of a particular VPT Session and over time. The evaluation process can be performed as often as necessary or desired.

In step 304, the user inputs and performance data from past VPT Sessions are analyzed. This data provides information that is useful for establishing parameters that select VPT Images 100 and VPT Sessions to use to evaluate the person's visual perception.

In step 306, a VPT Session is selected from a first group of potential VPT Sessions. VPTs within each VPT Session are used to collect data from the person regarding different aspects of the person's visual perception process to detect the existence of any physical or neural defects.

In step 308, once the VPT Session has been selected, parameters for the VPT Session are generated. These parameters define the VPT Images that are to be presented to the person, and in particular control the difficulty of the VPTs as well as other characteristics.

In step 310, a treatment phase is initiated for improving various aspects of the visual perception process of a person and alleviate visual perception deficiencies. The flow of the treatment phase is almost identical to that of the evaluation phase. In step 312, the user inputs from past VPT Sessions are analyzed. In step 314, a VPT Session is selected from a second group of VPT Sessions. This second group of VPT Sessions is different than the group described for the evaluation phase. In step 316, parameters are generated which again define the VPT Images that are to be presented to the person.

Figure 5:
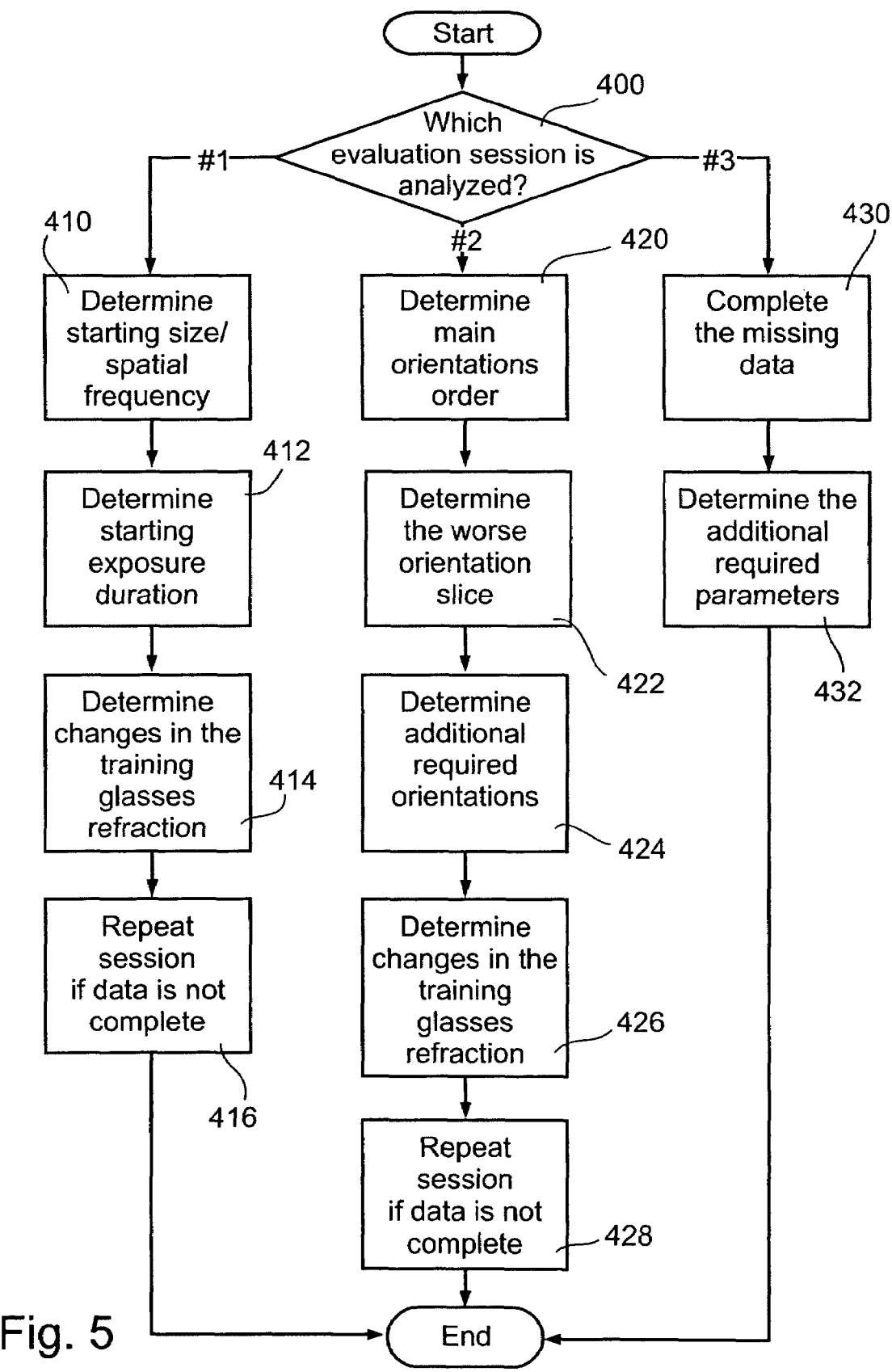
FIG. 5 is a flow chart illustrating the analysis in an evaluation session.

FIG. 5 is a flow chart illustrating the operations involved in the analysis of an evaluation session 400. Three such evaluation sessions are illustrated.

In the first evaluation session, a determination is made of the starting size/spatial frequency (step 410), and of the starting exposure duration (step 412). A determination is then made of any changes required in the refraction of the training glasses (step 414). The foregoing operations are repeated if the data is not complete (step 416).

In the second evaluation session, a determination is made of the main orientations order (step 420), of the worse orientation slice (step 422), and of any additional required orientations (step 424). A determination is then made whether any changes are required in the refraction of the training glasses (426). If the data is not complete, the foregoing operations are repeated (step 428).

In the third evaluation session, any missing data is completed (step 430), and a determination is made as to any additional required parameters (432).

Figure 6:
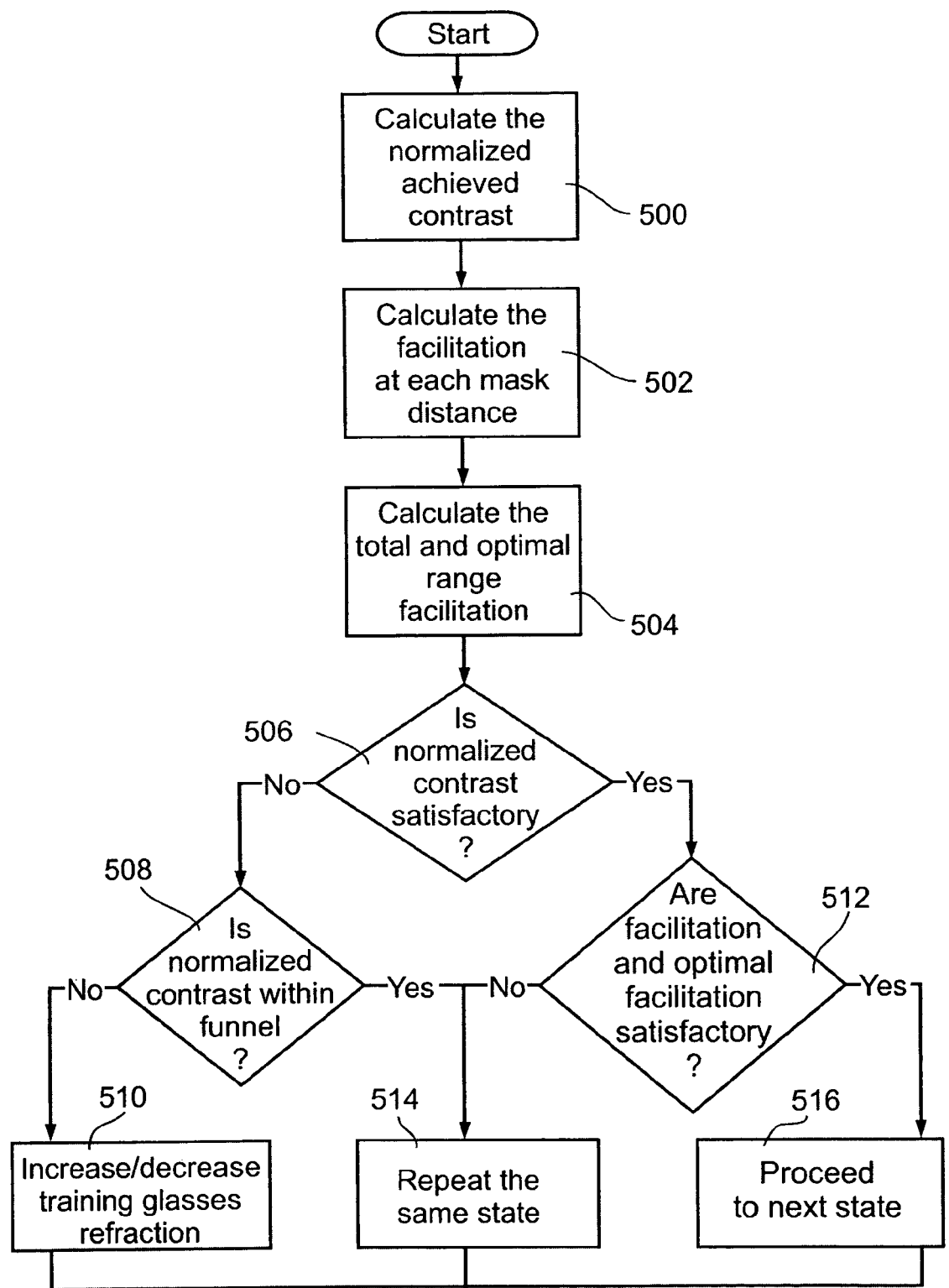
FIGS. 6 and 7 are flow charts illustrating the analysis in a treatment session.
Figure 7:
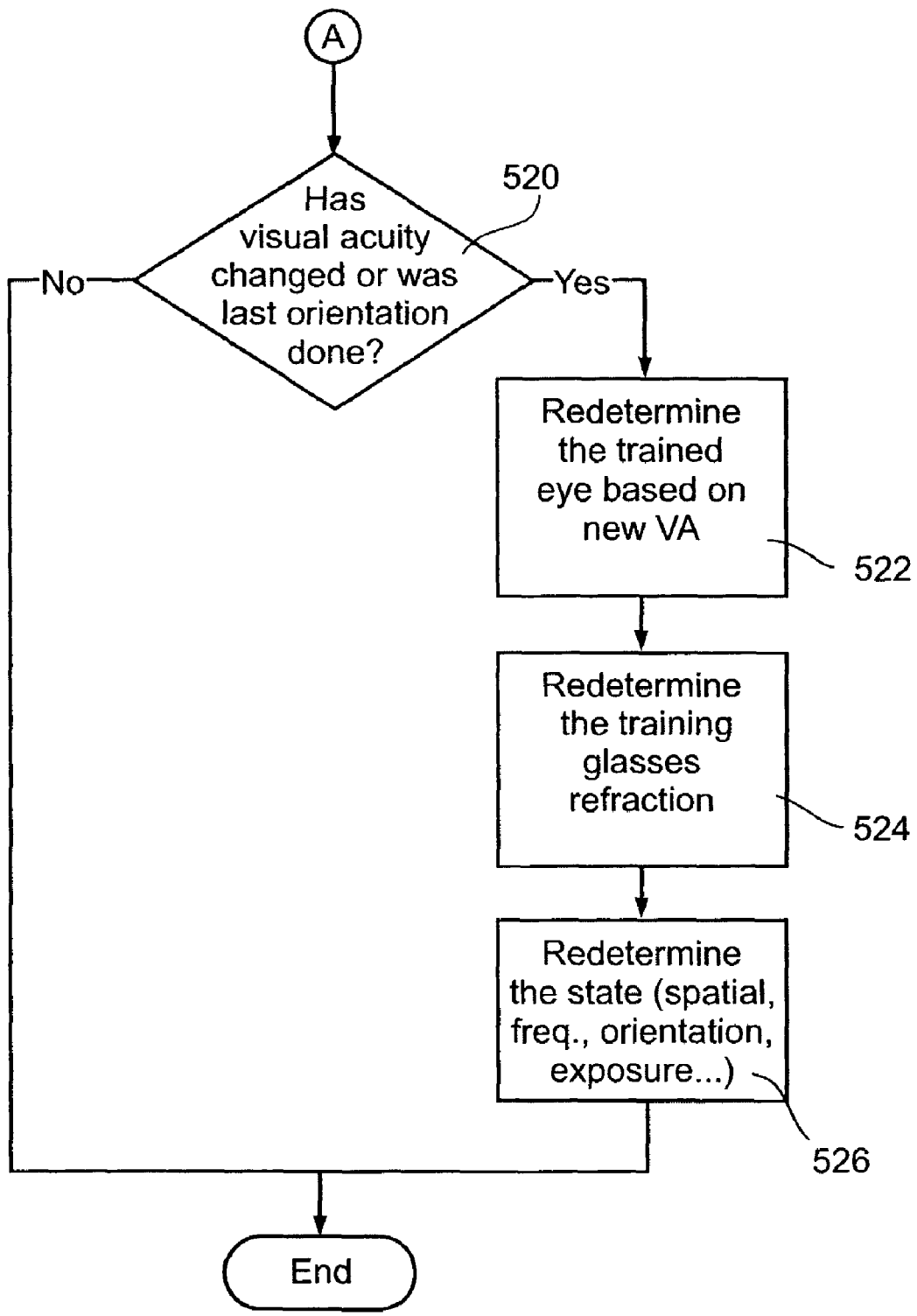

FIGS. 6 and 7 illustrate the operations involved in analyzing a treatment session. Thus, the first operations are to calculate the normalized achieved contrast (step 500), the facilitation at each mask distance (step 502), and the total and optimal range facilitation (step 504). A determination is then made as to whether the normalized contrast is satisfactory (step 506). If not, a determination is made as to whether the normalized contrast is within the desired funnel (step 508), and if not, the refraction of the training glasses is appropriately increased or decreased (step 510).

On the other hand, if in operation 506 the normalized contrast was found to be satisfactory, a determine is made as to whether the facilitation and optimal facilitation are satisfactory (step 512). If not, the same state is repeated (step 514), but if so, the program proceeds to the next state (step 516).

As seen in the flow chart of FIG. 7, after the foregoing operations have been performed in a treatment session, a determination is made as to whether the visual acuity has changed or whether the last orientation was done (step 520). If not, the analysis is completed, but if so, the trained eye is re-determined based on the new visual acuity (step 522), of any required changes in the refraction of the training glasses (step 524), and of the state, i.e., spatial frequency, orientation, exposure (step 526).

The foregoing operations are performed until the desired "contrast funnel" is achieved, i.e., the desired range of contrast levels a patient is expected to achieve in order to gain optimal visual improvement while undergoing the foregoing treatment.

While the invention has been described with respect to a preferred embodiment thereof, it will be appreciated that this is set forth merely for purposes of example, and that many other variations, modifications and applications of the invention may be made.

What is claimed is:

1. Apparatus for improving the visual perception ability of a person with respect to a particular eye condition of at least one eye, comprising:

a client terminal including a display device for displaying images to the person, and an input device for inputting responses by the person to images displayed in said display device;

and a processor system programmed such that in an evaluation phase, the processor controls said display device to display to the person a plurality of images selected to test the visual perception ability of the person with respect to at least one visual defect or inefficiency, and utilizes responses inputted by the person via said input device to select another plurality of images designed to further test the visual perception ability of the person with respect to at least one visual defect or inefficiency, and in a treatment phase, the processor controls said display device to display to the person said another plurality of images to thereby improve the visual perception ability of the person with respect to said detected visual defect or inefficiency, and utilizes responses inputted by the person via said input device to select another plurality of images designed to further improve the visual perception ability of the person with respect to said detected visual defect or inefficiency;

characterized in that said display device is a head-wearable display wearable over the eyes of said person and controlled by said processor system to display said plurality of images during both said evaluation phase and said treatment phase.

2. The apparatus according to claim 1, wherein said head-wearable display further includes earphones to be located over the ears of a person, and also controlled by said processor system to provide audio information to the person regarding the images displayed.

3. The apparatus according to claim 1, wherein said apparatus further includes training glasses or lenses to be worn by the person and having an increased or reduced refraction with respect to at least one eye of the person;

and wherein said head-wearable display further includes a holder for holding said training glasses or lenses in front of the at least one eye of the person during said treatment phase.

4. The apparatus according to claim 1, wherein said processor system includes a client processor in said client terminal, and a host processor in a host server serving a plurality of clients terminals;

and wherein said client processor and said input device are included in a hand-held portable unit.

5. The apparatus according to claim 4, wherein said client processor communicates with said head-wearable display via a wireless communication channel.

6. The apparatus according to claim 5, wherein said client processor communicates with said input device via a wireless communication channel.

7. The apparatus according to claim 5, wherein said head-wearable display further includes earphones to be located over the ears of a person and also controlled by said client processor to provide audio information to the person regarding the images displayed;

and wherein said client processor also communicates with said earphones via a wireless communication channel.

8. The apparatus according to claim 5, wherein said client processor communicates with said host processor via the Internet.

9. The apparatus according to claim 1, wherein said treatment phase includes a plurality of treatment sessions in each of which said processor system controls said head-wearable display to display a plurality of images designed to elicit responses from said person, which responses are used for selecting the plurality of images in a subsequent treatment session, such as to progressively improve the visual perception ability of the person with respect to the detected visual defect.

10. The apparatus according to claim 9, wherein said apparatus further includes training glasses or lenses to be worn by a person and having an increased or reduced refraction with respect to at least one eye of a person;

and wherein the refraction of said training glasses or lenses is variable such that after each treatment session, the refraction may be increased, decreased, or permitted to remain the same for the next treatment session, as determined by said processor in order to progressively improve the visual perception ability of the person with respect to the detected visual defect.

11. The apparatus according to claim 1, wherein at least one predetermined parameter of the plurality of images displayed in one treatment session is varied by the processor system in a subsequent treatment session.

12. The apparatus according to claim 1, wherein said processor system is programmed to control said head-wearable display to display in each of said treatment sessions a plurality of visual perception tasks in each of which there is displayed to the person at least one image including stimuli designed to elicit a response useful for selecting at least one other image to be displayed in the subsequent visual perception task of the respective treatment session, such as to progressively improve the visual perception ability of the person with respect to the detected defect.

13. The apparatus according to claim 12, wherein said processor system is programmed to control said head-wearable display to display said visual perception tasks in at least some of said sessions in the treatment phase to include spatial frequency changes in which the special frequency of said stimuli is changed.

14. The apparatus according to claim 13, wherein said processor system is programmed to control said head-wearable display to change the spatial frequency of said stimuli by starting with lower spatial frequencies and progressively moving to higher spatial frequencies.

15. The apparatus according to claim 12, wherein said processor system is programmed to control said head-wearable display to change the orientation of said stimuli.

16. The apparatus according to claim 12, wherein said processor system is programmed to control said head-wearable display, in at least some of said treatment sessions in the treatment phase, to change the orientations of said stimuli by progressing them towards a distortion area in an astigmatic zone of the eye for treating an eye for astigmatism.

17. The apparatus according to claim 12, wherein said processor system is programmed to include in said treatment phase a sufficient number of treatment sessions to improve the person's contrast sensitivity function by the person achieving a desired range of contrast levels representing a desired contrast funnel.

18. The apparatus according to claim 9, wherein said evaluation phase includes a plurality of evaluation sessions in each of which said processor system controls said head-wearable display to display a plurality of images to elicit responses inputted via said input device and utilized by said processor system to select the plurality of images to be displayed in the next evaluation session.

19. The apparatus according to claim 1, wherein said processor system controls said head-wearable display to display a plurality of images, in at least the treatment phase, based on Gabor Functions.

20. The apparatus according to claim 1, wherein:
said apparatus includes a plurality of said client terminals each at the location of a person whose visual perception ability is to be improved;
said processor system includes a host processor in a remotely-located server;
said plurality of images are displayed in the respective head-wearable display of the respective client terminal in both said evaluation phase and said treatment phase;
and said inputted responses are communicated to said remotely-located server via the input device of the respective client terminal are utilized by said server to select said another plurality of images designed to treat the respective person with respect to the detected visual defect, and are communicated by said server to the respective client terminal at the location of the person whose visual perception ability is to be improved.

* * * * *